United States Patent
Doisaki et al.

(10) Patent No.: US 10,105,340 B2
(45) Date of Patent: Oct. 23, 2018

(54) COMPOSITION CONTAINING EICOSAPENTAENOIC ACID ALKYL ESTER, AND METHOD FOR PRODUCING SAME

(71) Applicants: NIPPON SUISAN KAISHA, LTD, Minato-ku, Tokyo (JP); MOCHIDA PHARMACEUTICAL CO., LTD., Shinjuku-ku, Tokyo (JP)

(72) Inventors: Nobushige Doisaki, Hachioji (JP); Shingo Arato, Hachioji (JP); Takuro Fukae, Hachioji (JP)

(73) Assignees: NIPPON SUISAN KAISHA, LTD., Tokyo (JP); MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/878,827

(22) Filed: Jan. 24, 2018

(65) Prior Publication Data

US 2018/0147176 A1  May 31, 2018

Related U.S. Application Data

(63) Continuation of application No. 15/511,757, filed as application No. PCT/JP2015/076380 on Sep. 17, 2015, now Pat. No. 9,918,953.

(30) Foreign Application Priority Data

Sep. 17, 2014  (JP) ................. 2014-188997

(51) Int. Cl.
| | |
|---|---|
| A61K 31/20 | (2006.01) |
| A61K 31/232 | (2006.01) |
| C07C 67/54 | (2006.01) |
| C07C 67/03 | (2006.01) |
| C11B 3/12 | (2006.01) |
| C07C 67/56 | (2006.01) |
| C11C 3/10 | (2006.01) |
| C07C 69/587 | (2006.01) |

(52) U.S. Cl.
CPC ............ *A61K 31/232* (2013.01); *C07C 67/03* (2013.01); *C07C 67/54* (2013.01); *C07C 67/56* (2013.01); *C07C 69/587* (2013.01); *C11B 3/12* (2013.01); *C11C 3/10* (2013.01)

(58) Field of Classification Search
CPC ....................................................... A61K 31/20
USPC ........................................................ 514/560
See application file for complete search history.

(56) References Cited

U.S. PATENT DOCUMENTS

| | | | |
|---|---|---|---|
| 5,840,944 A | 11/1998 | Furihata et al. | |
| 2001/0025112 A1 | 9/2001 | Fujita et al. | |
| 2013/0046020 A1 | 2/2013 | Liang et al. | |
| 2015/0252288 A1 | 9/2015 | Harata et al. | |
| 2017/0252315 A1* | 9/2017 | Doisaki ............... | A61K 31/232 |

FOREIGN PATENT DOCUMENTS

| | | |
|---|---|---|
| CN | 102391112 A | 3/2012 |
| EP | 0347509 A1 | 12/1989 |
| EP | 0460917 A2 | 11/1991 |
| EP | 3029021 A1 | 6/2016 |
| JP | H0441457 A | 2/1992 |
| JP | H05222392 A | 8/1993 |
| JP | 08100191 A | 4/1996 |
| JP | 2001303089 A | 10/2001 |
| JP | 2014510165 A | 4/2014 |
| WO | 2014054435 A1 | 4/2014 |

OTHER PUBLICATIONS

International Search Report corresponding to Application No. PCT/JP2015/076380; dated Dec. 15, 2015.
R.C. Wijesundera et. al., "Eicosapentaenoic acid geometrical isomer artifacts in heated fish oil esters," JAOCS; vol. 66, No. 12, Dec. 1989, pp. 1822-1830.
Svein A. Mjos et. al., "Geometrical isomerisation of eicosapentaenoic and docosahexaenois acid at high temperatures," European Journal of Lipid Science and Technology; Mar. 8, 2006, pp. 589-597.
Extended European Search Report corresponding to Application No. 15843040.5-1105/3196280 PCT/JP2015076380; dated Mar. 12, 2018.
Nobuhiro Zaima et al., "Effects of reactive radicals and heat on trans-isomerization of eicosapentaenoic acid," Division of Applied Biosciences, Kyoto University; 2007, vol. 73, No. 4, Aug. 1, 2007, pp. 897-901.

* cited by examiner

*Primary Examiner* — Raymond J Henley, III
(74) *Attorney, Agent, or Firm* — Cantor Colburn LLP

(57) ABSTRACT

Provided are: a composition containing 96-99 area % of eicosapentaenoic acid alkyl ester, the composition having an arachidonic acid alkyl ester content of 0.7 area % or less, and an eicosapentaenoic-acid-alkyl-ester mono-trans isomer content of 2.5 area % or less; and a method for producing a composition containing a high concentration of eicosapentaenoic acid alkyl ester, the method including performing precision distillation on a composition containing eicosapentaenoic acid alkyl ester, obtained by alkyl esterification of a raw material oil containing eicosapentaenoic acid, under a vacuum of 0.2 Ton or lower and a temperature of 190° C. or lower in the entire column, and performing a concentration treatment on the precision-distilled composition using chromatography.

14 Claims, No Drawings

US 10,105,340 B2

COMPOSITION CONTAINING EICOSAPENTAENOIC ACID ALKYL ESTER, AND METHOD FOR PRODUCING SAME

CROSS REFERENCE TO RELATED APPLICATIONS

The present application is a continuation of U.S. patent application Ser. No. 15/511,757 filed on Mar. 16, 2017, the entire contents of which are incorporated herein by reference and priority which is hereby claimed. Application Ser. No. 15/511,757 is the National stage of Application No. PCT/JP2015/076380, filed Sep. 17, 2015. Priority under 35 U.S.C. § 119(a) and 35 U.S.C. § 365(b) is hereby claimed from Japanese Application No. 2014-188997, filed Sep. 17, 2014, the disclosure of which are also incorporated herein by reference.

TECHNICAL FIELD

The present invention relates to compositions containing eicosapentaenoic acid alkyl esters, and methods for producing the same.

BACKGROUND ART

Being one of ω3 fatty acids, eicosapentaenoic acid (EPA; (5Z,8Z,11Z,14Z,17Z)-icosa-5,8,11,14,17-pentaenoic acid; hereinafter, the simple designation of "eicosapentaenoic acid" or "EPA" means this substance) is known as a component that shows an anti-arteriosclerosis action, a platelet aggregation suppressing action, a blood lipid lowering action, and so on. Being an ester form of eicosapentaenoic acid, ethyl eicosapentaenoate (also described as "EPA-E" or "ethyl icosapentate") is sold as a health food, switch OTC, a pharmaceutical, and so on.

On account of these outstanding functions of EPA, many methods to produce EPA or EPA-E have also been reported. For instance, it is known that when a mixture obtained from a natural oil or fat is subjected to rectification with three or more distillation columns under high vacuum, a fraction that substantially consists of only a $C_{20}$ fatty acid or an ester thereof is obtained and may be further refined to give a high-purity EPA or an ester form thereof (see JP HS-222392A).

On the other hand, it is known that the refined EPA-E also contains ethyl esters of fatty acids other than EPA derived from fish oil as the starting material, and impurities that are generated in the refining process. Exemplary fatty acids other than EPA derived from fish oil as the starting material include arachidonic acid that is classified as an ω6 fatty acid and considered to be a substance that is unfavorable to cardiovascular events, and saturated fatty acids. Known as impurities that are generated in the refining process are fatty acids that result from thermal denaturation in the refining process and in which the five cis double bonds of EPA have been partially isomerized to trans (e.g. European Journal of Lipid Science and Technology, 108 (2006) 589-597, "Geometrical isomerization of eicosapentaenoic and docosahexaenoic acid at high temperatures"; JAOCS, 66 (1989) 1822-1830, "Eicosapentaenoic acid geometrical isomer artifacts in heated fish oil esters").

SUMMARY OF INVENTION

Technical Problem

A need exists to develop an improved technique by which one can efficiently obtain compositions that contain eicosapentaenoic acid alkyl esters such as ethyl eicosapentaenoate at high purities and which have smaller contents of impurities.

An object, therefore, of the present invention is to provide eicosapentaenoic acid alkyl ester-containing compositions of reduced impurity contents. Another object of the present invention is to provide methods for producing such compositions. Yet another object of the present invention is to provide various applications of eicosapentaenoic acid alkyl ester-containing compositions

Solutions to Problem

The present inventors conducted intensive studies on these problems and have found that the process of refining ethyl eicosapentaenoate gives rise to impurities that have extremely similar structures to ethyl eicosapentaenoate and which are difficult to separate from ethyl eicosapentaenoate, and that there can be produced compositions in which the contents of these impurities are reduced and which contain eicosapentaenoic acid alkyl esters at high purities; the present invention has been completed on the basis of these findings. Impurities that have been identified by the present inventors' research include, for example, an ethyl ester of arachidonic acid (C20:4n-6) which has the same carbon number as ethyl eicosapentaenoate, other impurities having similar structures to ethyl eicosapentaenoate (respective ethyl esters of C20:0, C20:4n-3, C20:5n-3(5,9,11,14,17), C18:3n-3, C18:4n-3, C19:0, C19:5n-3, C21:5n-3, and C22:6n-3), and mono-trans isomers of ethyl eicosapentaenoate.

To be more specific, aspects of the present invention include, but are not limited to, the followings.

[1] An eicosapentaenoic acid alkyl ester-containing composition which, upon measurement by gas chromatography, comprises 96-99 area % of an eicosapentaenoic acid alkyl ester, wherein the content of an arachidonic acid alkyl ester is 0.7 area % or less, and the content of mono-trans forms of the eicosapentaenoic acid alkyl ester is 2.5 area % or less, 2.3 area % or less, 2.0 area % or less, 1.8 area % or less, or 1.5 area % or less.

[2] The composition of [1], wherein the sum of the contents of mono-trans forms and di-trans forms of the eicosapentaenoic acid alkyl ester is 2.5 area % or less, 2.3 area % or less, 2.0 area % or less, 1.8 area % or less, or 1.5 area % or less.

[3] The composition of [1], wherein the sum of the contents of mono-trans forms, di-trans forms and tri-trans forms of the eicosapentaenoic acid alkyl ester is 2.5 area % or less, 2.3 area % or less, 2.0 area % or less, 1.8 area % or less, or 1.5 area % or less.

[4] The composition of [1], wherein the sum of the contents of mono-trans forms, di-trans forms, tri-trans forms and tetra-trans forms of the eicosapentaenoic acid alkyl ester is 2.5 area % or less, 2.3 area % or less, 2.0 area % or less, 1.8 area % or less, or 1.5 area % or less.

[5] The composition of any one of [1]-[4], wherein the content of any one of the mono-trans forms of the eicosapentaenoic acid alkyl ester in which any one of the double bonds at 5-, 14-, and 17-positions thereof is trans is 0.5 area % or less, 0.4 area % or less, 0.3 area % or less, 0.2 area % or less, or 0.1 area % or less.

[6] The composition of any one of [1]-[5], wherein the content of a mono-trans form of the eicosapentaenoic acid alkyl ester in which the double bond at 11-position thereof is trans is 1.0 area % or less, 0.9 area % or less, 0.8 area % or less, 0.6 area % or less, 0.4 area % or less, 0.2 area % or less, or 0.1 area % or less.

[7] A composition which, upon measurement by gas chromatography under the following analytical conditions, comprises 96-99 area % of ethyl eicosapentaenoate, wherein the content of an ethyl arachidonate is 0.7 area % or less, and wherein the sum of the contents of substances whose relative retention times appear as peaks at about 0.955, 1.027, 1.062 or 1.077, with the mean retention time of ethyl eicosapentaenoate being taken as 1, is 2.5 area % or less, 2.3 area % or less, 2.0 area % or less, 1.8 area % or less, or 1.5 area % or less:

[gas chromatographic analysis conditions: GC-FID measurement conditions]
GC: 6890N (Agilent Technologies)
Column: DB-WAX (Agilent Technologies)
  30 m×0.25 mm ID, 0.25 μm in film thickness
Carrier gas: helium, 0.5 mL/min
Injection port: 300° C., 1 μL, Split (1:100)
Column temperature: 200° C. (constant)
Detector: FID, 300° C.
Makeup gas: nitrogen, 40 mL/min.

[8] The composition of any one of [1]-[7], wherein the arachidonic acid alkyl ester content is 0.1 area % or less or 0.05 area % or less.

[9] The composition of any one of [1]-[8], wherein the content of an eicosatetraenoic acid alkyl ester is 0.7 area % or less, 0.5 area % or less, 0.4 area % or less, 0.3 area % or less, 0.2 area % or less, or 0.1 area % or less.

[10] The composition of any one of [1]-[9], wherein the content of an octadecatetraenoic acid alkyl ester is 0.4 area % or less, 0.3 area % or less, 0.2 area % or less, or 0.1 area % or less.

[11] The composition of any one of [1]-[10], wherein the content of a nonadecapentaenoic acid alkyl ester is 0.2 area % or less, 0.15 area % or less, 0.1 area % or less, 0.05 area % or less, 0.049 area % or less, or 0.02 area % or less.

[12] The composition of any one of [1]-[11], wherein the eicosapentaenoic acid alkyl ester is ethyl eicosapentaenoate or methyl eicosapentaenoate.

[13] The composition of any one of [1]-[12], wherein the content of a n-nonadecanoic acid (C19:0) alkyl ester is 0.1 area % or less, 0.07 area % or less, 0.05 area % or less, or 0.02 area or less.

[14] The composition of any one of [1]-[13], wherein the content of an arachidic acid (C20:0) alkyl ester is 0.2 area % or less, 0.15 area % or less, 0.1 area % or less, 0.05 area % or less, or 0.02 area % or less.

[15] The composition of any one of [1]-[14], wherein the content of alkyl esters of saturated fatty acids is 0.5 area % or less, 0.3 area % or less, or 0.1 area % or less.

[16] The composition of any one of [1]-[15], wherein the content of an icosa-5,9,11,14,17-pentaenoic acid (C20:5n-3(5,9,11,14,17)) alkyl ester is 0.2 area % or less, 0.15 area % or less, 0.1 area % or less, 0.07 area % or less, 0.05 area % or less, or 0.02 area % or less.

[17] The composition of any one of [1]-[16], wherein the content of a henicosapentaenoic acid alkyl ester is 0.2 area % or less, 0.15 area % or less, 0.1 area % or less, 0.05 area % or less, 0.03 area % or less, or 0.02 area % or less.

[18] The composition of any one of [1]-[17], wherein the content of the eicosapentaenoic acid alkyl ester is 96-98 area %.

[19] The composition of any one of [1]-[18], wherein the content of a dihomo-γ-linolenic acid alkyl ester is 0.05 area % or less.

[20] The composition of any one of [1]-[19], wherein the content of alkyl esters of monounsaturated fatty acids with carbon number of 20 or more is 0.05 area % or less.

[21] A pharmaceutical composition comprising the eicosapentaenoic acid alkyl ester-containing composition of any one of [1]-[20] as an effective component.

[22] The pharmaceutical composition of [21] further comprising a pharmaceutically acceptable additive component.

[23] The pharmaceutical composition of [21] or [22] which is a therapeutic or prophylactic agent for at least one disease selected from the group consisting of arteriosclerosis, cerebral infarct, cardiovascular infarct, thrombosis, lifestyle-related diseases, allergies, inflammatory diseases, and cancers.

[24] A method for producing high-concentration ethyl eicosapentaenoate, comprising ethyl esterifying a feed oil containing eicosapentaenoic acid and thereafter performing distillation and chromatography, wherein the distillation is carried out by performing rectification with the degree of vacuum being 0.2 Torr or less and at a whole-column temperature of 190° C. or less, whereby the content of ethyl arachidonate is reduced while suppressing the generation of a trans form due to heat.

[25] A method for producing a high-concentration eicosapentaenoic acid alkyl ester-containing composition, which comprises performing rectification on an eicosapentaenoic acid alkyl ester-containing composition with the degree of vacuum being 0.2 Torr or less and at a whole-column temperature 190° C. or less, and performing a concentration treatment on the rectified composition using chromatography, the eicosapentaenoic acid alkyl ester-containing composition being obtained by alkyl esterifying a feed oil containing eicosapentaenoic acid.

[26] The method of [25], wherein the alkyl esterification is performed using a lower alcohol with carbon number 1 or carbon number 2.

[27] The method of any one of [24]-[26], wherein the eicosapentaenoic acid alkyl ester-containing composition of any one of [1]-[20] is obtainable by carrying out rectification and chromatography.

[28] The method of any one of [24]-[27], wherein the rectification is continuous rectification using two or more distillation columns.

[29] The method of any one of [24]-[28], wherein the chromatography is reverse-phased chromatography.

[30] The method of any one of [24]-[29], wherein the feed oil is an oil or fat derived from a marine product as a feed.

[31] Use of the eicosapentaenoic acid alkyl ester-containing composition of any one of [1]-[20] in the manufacture of foods.

[32] Use of the eicosapentaenoic acid alkyl ester-containing composition of any one of [1]-[20] in the manufacture of a pharmaceutical composition.

[33] The use of [32], wherein the pharmaceutical composition is a therapeutic or prophylactic agent for at least one disease selected from the group consisting of arteriosclerosis, cerebral infarct, cardiovascular infarct, thrombosis, lifestyle-related diseases, allergies, inflammatory diseases, and cancers.

[34] Use of the eicosapentaenoic acid alkyl ester-containing composition of any one of [1]-[20] as an effective component of a therapeutic or prophylactic agent for at least one disease selected from the group consisting of arteriosclerosis, cerebral infarct, cardiovascular infarct, thrombosis, lifestyle-related diseases, allergies, inflammatory diseases, and cancers.

[35] A method of disease prevention, treatment, or relief comprising administering the pharmaceutical composition of any one of [21]-[23] to a subject who is affected or at a risk of being affected with at least one disease selected from the group consisting of arteriosclerosis, cerebral infarct, cardiovascular infarct, thrombosis, lifestyle-related diseases, allergies, inflammatory diseases, and cancers.

Aspects of the present invention also include, but are not limited to, the followings.

(1) A composition which, upon measurement by gas chromatography, comprising 96-99 area % of ethyl eicosapentaenoate, wherein the content of an ethyl arachidonate is 0.7 area % or less, and the content of mono-trans forms of the ethyl eicosapentaenoate is 2.5 area % or less.

(2) The composition of (1), wherein the sum of the contents of mono-trans forms and di-trans forms of the ethyl eicosapentaenoate is 2.5 area % or less.

(3) The composition of (1), wherein the sum of the contents of mono-trans forms, di-trans forms and tri-trans forms of the ethyl eicosapentaenoate is 2.5 area % or less.

(4) The composition of (1), wherein the sum of the contents of mono-trans forms, di-trans forms, tri-trans forms and tetra-trans forms of the ethyl eicosapentaenoate is 2.5 area % or less.

(5) The composition of any of (1)-(4), wherein the content of any one of the mono-trans forms of the ethyl eicosapentaenoate in which any one of the double bonds at 5-, 14-, and 17-positions thereof is trans is 0.5 area % or less.

(6) The composition of any of (1)-(5), wherein the content of a mono-trans form of the ethyl eicosapentaenoate in which the double bond at 11-position thereof is trans is 1.0 area % or less.

(7) A composition which, upon measurement by gas chromatography under the following analytical conditions, comprises 96-99 area % of ethyl eicosapentaenoate, wherein the content of an ethyl arachidonate is 0.7 area % or less, wherein the sum of the contents of substances whose relative retention times appear as peaks at about 0.955, 1.027, 1.062 or 1.077, with the mean retention time of ethyl eicosapentaenoate being taken as 1, is 2.5 area % or less:

[gas chromatographic analysis conditions: GC-FID measurement conditions]
GC: 6890N (Agilent Technologies)
Column: DB-WAX (Agilent Technologies)
 30 m×0.25 mm ID, 0.25 μm in film thickness
Carrier gas: helium, 0.5 mL/min
Injection port: 300° C., 1 μL, Split (1:100)
Column temperature: 200° C. (constant)
Detector: FID, 300° C.
Makeup gas: nitrogen, 40 mL/min.

(8) The composition of any of [1]-[7], wherein the content of a n-nonadecanoic acid (C19:0) ethyl ester is 0.1 area % or less.

(9) The composition of any of (1)-(8), wherein the content of an arachidic acid (C20:0) ethyl ester is 0.2 area % or less.

(10) The composition of any of (1)-(9), wherein the content of ethyl esters of saturated fatty acids is 0.5 area % or less.

(11) The composition of any of (1)-(10), wherein the content of an icosa-5,9,11,14,17-pentaenoic acid (C20:5n-3(5,9,11,14,17)) ethyl ester is 0.2 area % or less.

(12) The composition of any of (1)-(11), wherein the content of the ethyl eicosapentaenoate is 96-98 area %.

(13) A pharmaceutical composition comprising the composition of any of (1)-(12) as an effective component.

(14) A method for producing high-concentration ethyl eicosapentaenoate, wherein ethyl eicosapentaenoate is purified by ethyl esterifying a feed oil containing eicosapentaenoic acid and thereafter performing a distillation step and a chromatographic step, and wherein the distillation step is performed by performing rectification with the degree of vacuum being 0.2 Torr or less and at a whole-column temperature of 190° C. or less, whereby the content of ethyl arachidonate is reduced while suppressing the generation of a trans form due to heat.

(15) The method of (14), wherein the rectification is continuous rectification using two or more distillation columns.

(16) The method of (14) or (15), wherein the chromatographic step is a reverse-phased chromatographic step.

(17) A composition comprising 96 area % or more, 96-99 area % or 96-98 area % of ethyl eicosapentaenoate and 0.7 area % or less, 0.5 area % or less, 0.4 area % or less, 0.3 area % or less, 0.2 area % or less, or 0.1 area % or less of ethyl arachidonate.

(18) The composition of (17) which, upon measurement by gas chromatography under the foregoing analytical conditions, is such that the content of any one of substances whose relative retention times appear as peaks of about 0.955, 1.027 or 1.062, with the mean retention time of ethyl eicosapentaenoate being taken as 1, is 0.5 area % or less, 0.4 area % or less, 0.3 area % or less, 0.2 area % or less, or 0.1 area % or less

(19) The composition of (17) or (18) which, upon measurement by gas chromatography under the foregoing analytical conditions, is such that the content of a substance whose relative retention time appears as a peak of about 1.077, with the mean retention time of ethyl eicosapentaenoate being taken as 1, is 1.0 area % or less, 0.8 area % or less, 0.6 area % or less, 0.4 area % or less, 0.3 area % or less, 0.2 area % or less, or 0.1 area % or less.

(20) The composition of any of (17)-(19), wherein the content of α-linolenic acid (C18:3n-3) ethyl ester is 0.2 area % or less.

(21) A composition comprising 96-99 area % of ethyl eicosapentaenoate, wherein the content of ethyl arachidonate is 0.2 area % or less and the sum of the contents of mono-trans forms, di-trans forms, tri-trans forms and tetra-trans forms of the ethyl eicosapentaenoate is 2.5 area % or less.

(22) The composition of (21), wherein the content of ethyl esters of saturated fatty acids is 0.5 area % or less.

(23) The composition of (21) or (22), wherein the content of an ethyl ester of icosa-5,9,11,14,17-pentaenoic acid (C20:5n-3(5,9,11,14,17)) is 0.2 area % or less.

ADVANTAGEOUS EFFECTS OF INVENTION

It has been found in the present invention that one can produce compositions that are reduced in the contents of arachidonic acid alkyl esters having similar structures to eicosapentaenoic acid alkyl esters as well as mono-trans forms of eicosapentaenoic acid alkyl esters and which contain eicosapentaenoic acid alkyl esters at high purities. Since compositions in one embodiment of the present invention can even be produced on an industrial scale, they can advantageously be used as health foods, pharmaceuticals, etc. that need be mass-produced while having the safety feature.

Minimizing the content of arachidonic acid which is a typical o6 fatty acid means decreasing as much as possible the amount of the fatty acid which has functions contradictory to those of eicosapentaenoic acid alkyl esters. Hence, when the content of arachidonic acid is minimized, the functions of eicosapentaenoic acid alkyl esters can be effectively exhibited.

There is known a general relationship that an attempt to reduce the contents of arachidonic acid, etc. by distillation results in an increase of trans isomers which are the products of thermal denaturation. According to a method in one embodiment of the present invention, arachidonic acid and trans isomers of eicosapentaenoic acid which have such a relationship with eicosapentaenoic acid can both be reduced in content as compared with the conventional levels.

DESCRIPTION OF EMBODIMENTS

The word "step" as used herein does not mean an independent step only and even such cases as where clear distinction from other steps is not possible are encompassed by this term if the intended object of that step is attained. The amount of each component in a composition as recited herein is such that if the composition contains more than one substance that corresponds to each component, it means, unless otherwise specified, the sum amount of those substances which are present in the composition.

The numerical ranges as indicated herein by using "-" shall each refer to a range that includes the numerical value before it as the minimum and the numerical value after it as the maximum. The term "or less" or "less than" as used herein with reference to percentages includes, unless the lower limit is specifically cited, the case of 0%, i.e. "not contained" or, alternatively, it means a range that includes values undetectable by current means.

In the case where a numerical range specifying only one or more upper limits and another numerical range specifying only one or more lower limits, both referring to the same subject, are recited herein, it should be understood that unless otherwise noted, a numerical range as established by combining any upper limit that is selected from said one or more upper limits with any lower limit that is selected from said one or more lower limits is also included in one mode of the present invention.

The "oil(s)" or "oil(s) and fat(s)" as used herein includes not only those which solely consist of triglycerides but also crude oils which, in addition to triglycerides as a major component, contain other lipids such as diglycerides, monoglycerides, phospholipids, cholesterols, and free fatty acids. The "oil(s)" or "oil(s) and fat(s)" means compositions that contain these lipids.

The term "fatty acids" includes not only free saturated or unsaturated fatty acids on their own but also those fatty acids as constituent units which are internally contained in free saturated or unsaturated fatty acids, saturated or unsaturated fatty acid alcohol esters, triglycerides, diglycerides, monoglycerides, phospholipids, steryl esters, or the like; the fatty acids may hence be rewritten as constituent fatty acids. In the specification, unless otherwise noted, the forms of compounds containing fatty acids may sometimes be omitted. The forms of compounds containing fatty acids may include the free fatty acid form, the fatty acid alcohol ester form, the glycerol ester form, phospholipid's form, the steryl ester form, and so on. Compounds containing the same fatty acid may be contained as a single form in oils or they may be contained as a mixture of two or more forms.

When denoting fatty acids, a convenient way of numerical expression in which the carbon number, the number of double bonds and the positions of double bonds are represented by means of numbers and letters of alphabet may sometime be used. For instance, a saturated fatty acid with carbon number 20 can be denoted as "C20:0", a monounsaturated fatty acid with carbon number 18 denoted as "C18:1" and so on, and arachidonic acid denoted as "C20:4, n-6" and so on. The symbol "n-" shows the position of a double bond as counted from the methyl end of a fatty acid; for instance, "n-6" shows that a double bond is at the $6^{th}$ position as counted from the methyl end of a fatty acid. This method is well known to persons skilled in the art and fatty acids that are denoted in accordance with this method can be easily identified by any person skilled in the art.

The "crude oil" as used herein means an oil that is a mixture of the aforementioned lipids and which is as extracted from organisms. The "refined oil" as used herein means an oil that is obtained from a crude oil by performing a crude oil refining treatment in which at least one oil or fat refining step selected from the group consisting of a degumming step, a deacidifying step, a decolorizing step, and a deodorizing step is applied to the crude oil to remove any substances other than the end product, such as phospholipids and sterols.

<Compositions>
Makeup

Compositions in one embodiment of the present invention contain the following amounts of eicosapentaenoic acid alkyl esters (hereinafter referred to as EPA alkyl esters) like ethyl eicosapentaenoate (EPA-E) and may contain the following amounts of one or more other components, namely, impurities.

Briefly, a composition in one mode of the present invention is an eicosapentaenoic acid alkyl ester-containing composition which, upon measurement by gas chromatography, comprises 96-99 area % of an eicosapentaenoic acid alkyl ester, wherein the content of an arachidonic acid alkyl ester is 0.7 area % or less, and the content of mono-trans forms of the eicosapentaenoic acid alkyl ester is 2.5 area % or less.

The composition in one embodiment of the present invention contains 96-99 area %, preferably contains 96-98 area %, of the EPA alkyl ester. With the EPA alkyl ester content being 96 area % or more, the composition is preferably used in cases such as pharmaceutical applications where EPA alkyl esters of high purity are required. With the EPA alkyl ester content being 99 area % or less, the composition contains the EPA alkyl ester at high concentration and yet the yield of the EPA alkyl ester in the concentrating step can be maintained in a satisfactory range; this may be considered to be reasonable from an industrial viewpoint.

The alkyl group in EPA alkyl esters is an alkyl group that derives from those lower alcohols which are commonly used in alkyl esterification of fatty acids. Examples of the alkyl group in EPA alkyl esters preferably include an alkyl group with carbon number 1 or carbon number 2, and specifically include a methyl group and an ethyl group. Exemplary EPA alkyl esters include EPA ethyl (EPA-E) and EPA methyl (EPA-M).

Isomers as impurity that may be contained in the composition in one embodiment of the present invention include mono-trans forms in which one of the five cis double bonds that the EPA alkyl ester has has been converted to trans. The content of these mono-trans forms in the composition in one embodiment of the present invention can be 2.5 area % or less, 2.3 area % or less, 2.0 area % or less, 1.8 area % or less, or 1.5 area % or less. In the case where the mono-trans forms are contained in smaller amounts, the composition in one embodiment of the present invention contains the EPA alkyl ester at higher concentrations and can exhibit the functionality of the EPA alkyl ester more effectively.

Other isomers as impurity are di-trans forms in which two of the five cis double bonds that the EPA alkyl ester has have been converted to trans. The sum of the contents of the mono- and di-trans forms in the composition in one embodiment of the present invention can be adjusted to 2.5 area % or less, 2.3 area % or less, 2.0 area % or less, 1.8 area % or less, or 1.5 area % or less.

In the case where the mono-trans forms and the di-trans forms are contained in smaller amounts of sum, the composition in one embodiment of the present invention contains the EPA alkyl ester at higher concentrations and can exhibit the functionality of the EPA alkyl ester more effectively.

Still other isomers as impurity are tri-trans forms in which three of the five cis double bonds that the EPA alkyl ester has have been converted to trans. The sum of the contents of these mono-, di- and tri-trans forms in the composition in one embodiment of the present invention can be adjusted to 2.5 area % or less, 2.3 area % or less, 2.0 area % or less, 1.8 area % or less, or 1.5 area % or less.

Yet other isomers as impurity are tetra-trans forms in which four of the five cis double bonds that the EPA alkyl ester has have been converted to trans. The sum of the contents of these mono-, di-, tri- and tetra-trans forms in the composition in one embodiment of the present invention can be adjusted to 2.5 area % or less, 2.3 area % or less, 2.0 area % or less, 1.8 area % or less, or 1.5 area % or less.

As mentioned above, if two or more of the mono-, di-, tri- and tetra-trans forms are contained in smaller amounts of sum, the composition in one embodiment of the present invention contains the EPA alkyl ester at higher concentrations and can exhibit the functionality of the EPA alkyl ester more effectively.

The isomers as impurity in the composition in one embodiment of the present invention may be exemplified by mono-trans forms in which one of the five cis double bonds that EPA-E has has been converted to trans. The content of these mono-trans forms that may be contained in the composition in one embodiment of the present invention can be 2.5 area % or less, 2.3 area % or less, 2.0 area % or less, 1.8 area % or less, or 1.5 area % or less.

Other isomers as impurity may be exemplified by di-trans forms in which two of the five cis double bonds that EPA-E has have been converted to trans. The sum of the contents of the mono- and di-trans forms that may be contained in the composition in one embodiment of the present invention can be 2.5 area % or less, 2.3 area % or less, 2.0 area % or less, 1.8 area % or less, or 1.5 area % or less.

Still other isomers as impurity may be exemplified by tri-trans forms in which three of the five cis double bonds that EPA-E has have been converted to trans. The sum of the contents of these mono-, di- and tri-trans forms that may be contained in the composition in one embodiment of the present invention can be 2.5 area % or less, 2.3 area % or less, 2.0 area % or less, 1.8 area % or less, or 1.5 area % or less.

Yet other isomers as impurity may be exemplified by tetra-trans forms in which four of the five cis double bonds that the EPA alkyl ester has have been converted to trans. The sum of the contents of the mono-, di-, tri- and tetra-trans forms that may be contained in the composition in one embodiment of the present invention can be 2.5 area % or less, 2.3 area % or less, 2.0 area % or less, 1.8 area % or less, or 1.5 area % or less.

The composition in one embodiment of the present invention can be adapted to be such that the sum of the contents of the mono-, di-, tri- and tetra-trans forms as described above is 1.417 area % or more. If the composition contains the mono-, di-, tri- and tetra-trans forms in amounts no smaller than the specified value, other fatty acids that differ in structure from EPA tend to be contained in smaller amounts, depending on the contents of these isomers. If the composition contains these isomers in amounts no smaller than the specified value, the contents of other fatty acids that are difficult to separate from EPA, in particular, arachidonic acid alkyl esters tend to be small, with the result that the composition has a better balance in content between the EPA alkyl ester and other fatty acid alkyl esters that tend to separate from the same with difficulty and there is also a tendency for improvement in productivity.

When the double bonds in a cis form of the EPA alkyl ester receive heat during distillation, one double bond first turns to a trans form and upon further application of heat, di-, tri- and tetra-trans forms will result. Hence, if the generation of the mono-trans form can be suppressed, the generation of further trans forms can also be suppressed.

If distillation is conducted at a whole-column temperature of 190° C. or less, isomers of the EPA alkyl ester may sometimes result. For instance, as will be shown in the Examples, the isomers that result when distillation is conducted at a whole-column temperature of 190° C. or less are, as shown in the Examples, mono-trans forms in which any one of the double bonds at 5-, 11-, 14-, and 17-positions of EPA-E has been converted to trans.

In the composition in one embodiment of the present invention, the content of any one of mono-trans forms of the EPA alkyl ester in which any one of the double bonds at 5-, 14-, and 17-positions thereof is trans can be 0.5 area % or less, 0.4 area % or less, 0.3 area % or less, 0.2 area % or less, or 0.1 area % or less.

In the composition in one embodiment of the present invention, the content of a mono-trans form of the EPA alkyl ester in which the double bond at 11-position thereof is trans can be 1.0 area % or less, 0.9 area % or less, 0.8 area % or less, 0.6 area % or less, 0.4 area % or less, 0.2 area % or less, or 0.1 area % or less.

In the composition in one embodiment of the present invention, the content of any one of mono-trans forms of EPA-E, for example, in which any one of the double bonds at 5-, 14-, and 17-positions thereof is trans can be 0.5 area % or less, 0.4 area % or less, 0.3 area % or less, 0.2 area % or less, or 0.1 area % or less.

In the composition in one embodiment of the present invention, the content of a mono-trans form of EPA-E, for example, in which the double bond at 11-position thereof is trans can be 1.0 area % or less, 0.9 area % or less, 0.8 area % or less, 0.6 area % or less, 0.4 area % or less, 0.2 area % or less, or 0.1 area % or less.

In the case where the content of the mono-trans form with any one of the double bonds at 5-, 14-, and 17-positions being trans as mentioned above is of smaller values as mentioned above, or in the case where the content of the mono-trans form with the double bond at 11-position being trans is of smaller values as mentioned above, the composition in one embodiment of the present invention contains the EPA alkyl ester such as EPA-E at higher concentrations and can exhibit the functionality of the EPA alkyl ester such as EPA-E more effectively. In the case where the contents of the trans forms which have low boiling points and tend to become turbid or easily solidify at low temperatures are low, the composition of interest tends to show a good handling property at low temperatures.

In the present invention, "area %" is an index for the relative content of a component at a respective peak which is determined as follows: in a chart from the analysis of a composition using gas chromatography equipped with a flame ionization detector (FID), the peaks for respective components are identified and the peak areas of respective fatty acids are determined using Agilent ChemStation integration algorithm (Revision C.01.03 [37], Agilent Technologies), with the proportion of each peak area to the total sum of the fatty acid peak areas representing the relative content of the component at that peak. In the field of oil chemistry, area % is used as being substantially synonymous with wt %. Refer to Standard Methods for the Analysis of Fats, Oils and Related Materials, 2013 Edition (specified by Japan's Oil Chemists' Society (JOCS)) under 2.4.2.1-2013, Fatty Acids Makeup (FID gas chromatography at constant temperature) and also under 2.4.2.2-2013, Fatty Acids Makeup (FID gas chromatography at increasing temperature). The analytical conditions for gas chromatography are as follows.

In the case where the EPA alkyl ester is EPA-E, each of compounds identified as a mono-trans form of EPA-E can be such that the retention times of its peak under the following gas chromatographic measurement conditions will show the numerical value cited in Table 1 in Example 1. In the present invention, the relative retention time is expressed by a number obtained by dividing the actual retention time of each peak in gas chromatographic measurement by the retention time for ethyl eicosapentaenoate. In other words, the relative retention time represents the relative retention time of each peak, with the retention time of ethyl eicosapentaenoate being taken as 1. While the values of measurement for the retention times of respective peaks will scatter somewhat either from measurement to measurement or depending on the concentrations of components contained in a sample, such scattering will lie within ±0.01 when expressed in terms of relative retention time. The term "about" as used herein with respect to the relative retention time means that the range of this scattering is included.

GC-FID Measurement Conditions
GC: 6890N (Agilent Technologies)
   Column: DB-WAX (Agilent Technologies)
   30 m×0.25 mm ID, 0.25 μm in film thickness
   Carrier gas: helium, 0.5 mL/min
   Injection port: 300° C., 1 μL, Split (1:100)
   Column temperature: 200° C. (constant)
Detector: FID, 300° C.
Makeup gas: nitrogen 40 mL/min.

In the case of a composition wherein the EPA alkyl ester is EPA-E, the sum of the contents of substances whose relative retention times appear as peaks at about 0.955, 1.027, 1.062 or 1.077, with the mean retention time of ethyl eicosapentaenoate being taken as 1, can be 2.5 area % or less, 2.3 area % or less, 2.0 area % or less, 1.8 area % or less, or 1.5 area % or less.

In the case of the composition wherein the EPA alkyl ester is EPA-E, the sum of the contents of substances whose relative retention times appear as peaks at about 0.955, 1.027, 1.062 or 1.077, with the mean retention time of ethyl eicosapentaenoate being taken as 1, can be 1.417 area % or more.

In a composition according to one embodiment of the present invention, exemplary impurities include saturated or unsaturated fatty acid alkyl esters with carbon number 18 or more, such as arachidonic acid alkyl esters. The saturated or unsaturated fatty acid alkyl esters with carbon number 18 or more have similar or extremely similar structures to the EPA alkyl esters and as a general tendency, they are difficult to separate from the EPA alkyl esters in the distillation step and the chromatographic step.

The alkyl groups in the saturated or unsaturated fatty acid alkyl esters with carbon number 18 or more are alkyl groups derived from lower alcohols that are commonly used in the alkyl esterification of fatty acids. Exemplary alkyl groups in the saturated or unsaturated fatty acid alkyl esters with carbon number 18 or more preferably include an alkyl group of carbon number 1 or carbon number 2 and specifically include an ethyl group and a methyl group. For instance, exemplary saturated or unsaturated fatty acid alkyl esters with carbon number 18 or more include saturated or unsaturated fatty acid ethyl esters with carbon number 18 or more, and saturated or unsaturated fatty acid methyl esters with carbon number 18 or more. The same applies to the alkyl groups in the specific examples described below of saturated or unsaturated fatty acid alkyl esters with carbon number 18 or more.

In a composition in one embodiment of the present invention, the content of "an arachidonic acid alkyl ester" (C20:4n-6 alkyl ester, (5Z,8Z,11Z,14Z)-5,8,11,14-icosatetraenoic acid alkyl ester) is 0.7 area % or less; more preferably, it may be 0.5 area % or less, 0.4 area % or less, 0.3 area % or less, 0.2 area % or less, even more preferably 0.1 area % or less, or 0.05 area % or less.

In a composition in one embodiment of the present invention, the content of "an arachidonic acid ethyl ester" (C20:4n-6 ethyl ester, ethyl (5Z,8Z,11Z,14Z)-5,8,11,14-icosatetraenoate) is 0.7 area % or less; more preferably, it may be 0.5 area % or less, 0.4 area % or less, 0.3 area % or less, 0.2 area % or less, even more preferably 0.1 area % or less, or 0.05 area % or less.

Thus, in the composition in one embodiment of the present invention, by reducing the content of arachidonic acid, which is a typical ο6 fatty acid, to the lowest possible level as described above, the functions of EPA alkyl esters such as EPA-E can be exhibited effectively.

Impurities other than arachidonic acid alkyl esters that are contained in the composition in one embodiment of the present invention may, for example, include the following. These mainly have similar structures to the EPA alkyl esters and are considered to be substances that are difficult to separate from the EPA alkyl esters in the chromatographic step. Since compositions in respective embodiments of the present invention have low contents of one or more of these impurities, they may contain the EPA alkyl esters at high levels.

In a composition in one embodiment of the present invention, the content of "C20:5n-3(5,9,11,14,17) alkyl ester" (icosa-5,9,11,14,17-pentaenoic acid alkyl ester) may be 0.2 area % or less, 0.15 area % or less, 0.1 area % or less, 0.07 area % or less, 0.05 area % or less, or 0.02 area % or less. For instance, in the composition in one embodiment of the present invention, the content of "C20:5n-3(5,9,11,14,17) ethyl ester" (icosa-5,9,11,14,17-pentaenoic acid ethyl ester) may be 0.2 area % or less, 0.15 area % or less, 0.1 area % or less, 0.07 area % or less, 0.05 area % or less, or 0.02 area % or less.

In a composition in one embodiment of the present invention, the content of "C18:3n-3 alkyl ester" (a-linolenic acid alkyl ester, (9Z,12Z,15Z)-9,12,15-octadecatrienoic acid alkyl ester) may be 0.2 area % or less, 0.15 area % or less, 0.1 area % or less, 0.05 area % or less, or 0.02 area % or less. For instance, in the composition in one embodiment of the present invention, the content of "C18:3n-3 ethyl ester" (ethyl a-linolenate, ethyl (9Z,12Z,15Z)-9,12,15-octadecatrienoate) may be 0.2 area % or less, 0.15 area % or less, 0.1 area % or less, 0.05 area % or less, or 0.02 area % or less.

In a composition in one embodiment of the present invention, the content of "C18:4n-3 alkyl ester" (stearidonic acid alkyl ester, (6Z,9Z,12Z,15Z)-6,9,12,15-octadecatetraenoic acid alkyl ester) may be 0.4 area % or less, 0.3 area % or less, 0.2 area % or less, or 0.1 area % or less. For instance, in the composition in one embodiment of the present invention, the content of "C1 8:4n-3 ethyl ester" (ODTA-E, ethyl stearidonate, ethyl (6Z,9Z,12Z,15Z)-6,9,12,15-octadecatetraenoate) may be 0.4 area % or less, 0.3 area % or less, 0.2 area % or less, or 0.1 area % or less.

Since the C18:4n-3 alkyl ester is known as a functional component, a composition having lower contents of the C18:4n-3 alkyl ester such as C18:4n-3 ethyl ester will be affected less by an additional function that is added to itself. Hence, when using this composition as a functional composition based on the EPA alkyl ester, one may have a smaller need to consider other functions and the composition can be handled with ease.

In a composition in one embodiment of the present invention, the content of "C19:5n-3 alkyl ester" (nonadecapentaenoic acid alkyl ester) may be 0.2 area % or less, 0.15 area % or less, 0.1 area % or less, 0.05 area % or less, 0.049 area % or less, or 0.02 area % or less. For instance, in the composition in one embodiment of the present invention, the content of "C19:5n-3 ethyl ester" (NDPA-E, ethyl nonadecapentaenoate) may be 0.2 area % or less, 0.15 area % or less, 0.1 area % or less, 0.05 area % or less, 0.049 area % or less, or 0.02 area % or less.

Since the C19:5n-3 alkyl ester is known as a functional component, a composition having lower contents of the C19:5n-3 alkyl ester such as C19:5n-3 ethyl ester will be affected less by an additional function that is added to itself. Hence, when using this composition as a functional composition based on the EPA alkyl ester, one may have a smaller need to consider other functions and the composition can be handled with ease.

In a composition in one embodiment of the present invention, the content of "C20:4n-3 alkyl ester" (eicosatetraenoic acid alkyl ester) may be 0.7 area % or less, 0.5 area % or less, 0.4 area % or less, 0.3 area % or less, 0.2 area % or less, or 0.1 area % or less. For instance, in the composition in one embodiment of the present invention, the content of "C20:4n-3 ethyl ester" (ETA-E, ethyl eicosatetraenoate) may be 0.7 area % or less, 0.5 area % or less, 0.4 area % or less, 0.3 area % or less, 0.2 area % or less, or 0.1 area % or less.

Since the C20:4n-3 alkyl ester is known as a functional component, a composition having lower contents of the C20:4n-3 alkyl ester such as C20:4n-3 ethyl ester will be affected less by an additional function that is added to itself. Hence, when using this composition as a functional composition based on the EPA alkyl ester, one may have a smaller need to consider other functions and the composition can be handled with ease.

In a composition in one embodiment of the present invention, the content of "C21:5n-3 alkyl ester" (henicosapentaenoic acid alkyl ester) may be 0.2 area % or less, 0.15 area % or less, 0.1 area % or less, 0.05 area % or less, 0.03 area % or less, or 0.02 area % or less. For instance, in the composition in one embodiment of the present invention, the content of "C21:5n-3 ethyl ester" (HPA-E, ethyl henicosapentaenoate) may be 0.2 area % or less, 0.15 area % or less, 0.1 area % or less, 0.05 area % or less, 0.03 area % or less, or 0.02 area % or less.

Since the C21:5n-3 alkyl ester is known as a functional component, a composition having lower contents of the C21:5n-3 alkyl ester such as C21:5n-3 ethyl ester will be affected less by an additional function that is added to itself. Hence, when using this composition as a functional composition based on the EPA alkyl ester, one may have a smaller need to consider other functions and the composition can be handled with ease.

Fish oil contains saturated fatty acids with carbon numbers of 14-22 but in applications to the cardiovascular system, intake of saturated fatty acids is preferably avoided, so the content of saturated fatty acids in a composition in one embodiment of the present invention is preferably as low as possible. The sum of the contents of alkyl esters of saturated fatty acids may be 0.5 area % or less, 0.3 area % or less, or 0.1 area % or less. For instance, in the composition in one embodiment of the present invention, the sum of the contents of ethyl esters of saturated fatty acids may be 0.5 area % or less, 0.3 area % or less, or 0.1 area % or less.

In a composition in one embodiment of the present invention, the content of "C19:0 alkyl ester" (n-nonadecanoic acid alkyl ester) among saturated fatty acids may be 0.1 area % or less, 0.07 area % or less, 0.05 area % or less, or 0.02 area % or less. In the composition in one embodiment of the present invention, the content of "C19:0 ethyl ester" (ethyl n-nonadecanoate), for example, may be 0.1 area % or less, 0.07 area % or less, 0.05 area % or less, or 0.02 area % or less.

In a composition in one embodiment of the present invention, the content of "C20:0 alkyl ester" (arachidic acid alkyl ester) among saturated fatty acids may be 0.2 area % or less, 0.15 area % or less, 0.1 area % or less, 0.05 area % or less, or 0.02 area % or less. For instance, in the composition in one embodiment of the present invention, the content of "C20:0 ethyl ester" (ethyl arachidate) may be 0.2 area % or less, 0.15 area % or less, 0.1 area % or less, 0.05 area % or less, or 0.02 area % or less.

The composition in one embodiment of the present invention suffices to have low contents of fatty acids other than the EPA alkyl ester and the above-mentioned fatty acids. This enables the EPA alkyl ester to be contained at higher levels and in the case of using this composition as a functional composition based on the EPA alkyl ester, the need to consider other functions can be reduced.

Other fatty acids may include alkyl esters of monounsaturated fatty acids (MUFA) with carbon number 20 and more, and in a composition in one embodiment of the present invention, the content of MUFA alkyl esters may be 0.05 area % or less. For instance, in the composition in one embodiment of the present invention, the sum of the contents of MUFA ethyl esters such as "C20: 1n-11 ethyl ester" (ethyl gadoleate), "C20: 1n-9 ethyl ester" (ethyl gondoate), "C22: 1n-11 ethyl ester" (ethyl cetoleate), and "C22: 1n-9 ethyl ester" (ethyl erucate) may be 0.05 area % or less.

As for still other fatty acids, the content of "C20:3n-6 alkyl esters" (dihomo-γ-linolenic acid alkyl esters, or DGLA alkyl esters) may be 0.05 area % or less. For instance, in a composition in one embodiment of the present invention, the content of "C20:3n-6 ethyl ester" (ethyl dihomo-γ-linolenate, or DGLA ethyl ester) may be 0.05 area % or less. Compositions having low contents of n-6 fatty acids which might exhibit converse actions to EPA can satisfactorily exhibit the functions based on EPA alkyl esters.

As for yet other fatty acids, the content of "C22:6n-3 alkyl esters" (docosahexaenoic acid alkyl esters) may be 0.1 area % or less, 0.05 area % or less, or 0.03 area % or less. For instance, in a composition in one embodiment of the present invention, the content of "C22:6n-3 ethyl ester" (ethyl docosahexaenoate, or DHA ethyl ester) may be 0.1 area % or less, 0.05 area % or less, or 0.03 area % or less.

Since the C22:6n-3 alkyl esters are known as functional components, a composition having lower contents of the C22:6n-3 alkyl ester such as C22:6n-3 ethyl ester will be affected less by an additional function that is added to itself. Hence, when using this composition as a functional composition based on the EPA alkyl ester, one may have a smaller need to consider other functions and the composition can be handled with ease.

One embodiment of the present invention can include any of the following compositions, for example, with which the functions of EPA alkyl esters are obtained more effectively:

(1) An eicosapentaenoic acid alkyl ester-containing composition which, upon measurement by gas chromatography, comprises 96-99 area % of an EPA alkyl ester such as EPA-E, wherein the content of an alkyl arachidonate such as ethyl arachidonate is 0.1 area % or less or 0.05 area % or less, and the content of mono-trans forms of the eicosapentaenoic acid alkyl ester such as EPA-E is 2.5 area % or less, 2.3 area % or less, 2.0 area % or less, 1.8 area or less, or 1.5 area % or less.

(2) An eicosapentaenoic acid alkyl ester-containing composition which, upon measurement by gas chromatography, comprises 96-99 area % of an EPA alkyl ester such as EPA-E, wherein the content of an alkyl arachidonate such as ethyl arachidonate is 0.7 area % or less, and the content of mono-trans forms of the eicosapentaenoic acid alkyl ester such as EPA-E is 1.417 area % or more but 2.5 area % or less, 2.3 area % or less, 2.0 area % or less, 1.8 area % or less, or 1.5 area % or less.

(3) An eicosapentaenoic acid alkyl ester-containing composition which, upon measurement by gas chromatography under the following analytical conditions, comprises 96-99 area % of EPA-E, wherein the content of an ethyl arachidonate is 0.1 area % or less or 0.05 area % or less, and wherein the sum of the contents of substances whose relative retention times appear as peaks at about 0.955, 1.027, 1.062 or 1.077, with the mean retention time of EPA-E being taken as 1, is 2.5 area % or less, 2.3 area % or less, 2.0 area % or less, 1.8 area % or less, or 1.5 area % or less:

[gas chromatographic analysis conditions: GC-FID measurement conditions]
GC: 6890N (Agilent Technologies)
Column: DB-WAX (Agilent Technologies)
  30 m×0.25 mm ID, 0.25 μm in film thickness
Carrier gas: helium, 0.5 mL/min
Injection port: 300° C., 1 μL, Split (1:100)
Column temperature: 200° C. (constant)
Detector: FID, 300° C.
Makeup gas: nitrogen, 40 mL/min.

(4) An eicosapentaenoic acid alkyl ester-containing composition which, upon measurement by gas chromatography under the following analytical conditions, comprises 96-99 area % of EPA-E, wherein the content of an ethyl arachidonate is 0.7 area % or less, and wherein the sum of the contents of substances whose relative retention times appear as peaks at about 0.955, 1.027, 1.062 or 1.077, with the mean retention time of EPA-E being taken as 1, is 1.417 area % or more but 2.5 area % or less, 2.3 area % or less, 2.0 area % or less, 1.8 area % or less, or 1.5 area % or less:

[gas chromatographic analysis conditions: GC-FID measurement conditions]
GC: 6890N (Agilent Technologies)
Column: DB-WAX (Agilent Technologies)
  30 m×0.25 mm ID, 0.25 μm in film thickness
Carrier gas: helium, 0.5 mL/min
Injection port: 300° C., 1 μL, Split (1:100)
Column temperature: 200° C. (constant)
Detector: FID, 300° C.
Makeup gas: nitrogen, 40 mL/min.

(5) The composition of (1) above, wherein the content of mono-trans forms of the eicosapentaenoic acid alkyl ester such as EPA-E is 1.417 area % or more.

(6) The composition of (3) above, wherein the sum of the contents of substances whose relative retention times appear as peaks at about 0.955, 1.027, 1.062 or 1.077, with the mean retention time of EPA-E being taken as 1, is 1.417 area % or more.

(7) The composition of (2) above, wherein the content of ethyl arachidonate is 0.1 area % or less, or 0.05 area % or less.

(8) The composition of (4) above, wherein the content of ethyl arachidonate is 0.1 area % or less, or 0.05 area % or less.

The compositions of (1)-(8) above may further be such that the content of a DGLA alkyl ester such as DGLA ethyl ester is 0.05 area % or less, and in place of or in addition to the DGLA alkyl ester, the compositions may be such that the content of a MUFA alkyl ester such as MUFA ethyl ester is 0.05 area % or less.

In addition to the DGLA, MUFA or the combination of DGLA and MUFA, the compositions of (1)-(8) above may further satisfy, in combination therewith, at least one requirement selected from the group consisting of the following:

0.7 area % or less, 0.5 area % or less, 0.4 area % or less, 0.3 area % or less, 0.2 area % or less, or 0.1 area % or less of an eicosatetraenoic acid alkyl ester such as ethyl eicosatetraenoate;

0.4 area % or less, 0.3 area % or less, 0.2 area % or less, or 0.1 area % or less of an octadecatetraenoic acid alkyl ester such as ethyl octadecatetraenoate;

0.2 area % or less, 0.15 area % or less, 0.1 area % or less, 0.05 area % or less, 0.049 area % or less, or 0.02 area % or less of a nonadecapentaenoic acid alkyl ester such as ethyl nonadecapentaenoate;

0.1 area % or less, 0.07 area % or less, 0.05 area % or less, or 0.02 area % or less of a n-nonadecanoic acid (C19:0) alkyl ester such as ethyl n-nonadecanoate;

0.2 area % or less, 0.15 area % or less, 0.1 area % or less, 0.05 area % or less, or 0.02 area % or less of arachidic acid (C20:0) alkyl ester such as ethyl arachidate;

0.5 area % or less, 0.3 area % or less, or 0.1 area % or less of saturated fatty acid alkyl esters such as saturated fatty acid ethyl esters;

0.2 area % or less, 0.15 area % or less, 0.1 area % or less, 0.07 area % or less, 0.05 area % or less, or 0.02 area % or less of an icosa-5,9,11,14,17-pentaenoic acid (C20:5n-3(5,9,11,14,17) alkyl ester such as ethyl icosa-5,9,11,14,17-pentaenoate (C20:5n-3(5,9,11,14,17));

0.2 area % or less, 0.15 area % or less, 0.1 area % or less, 0.05 area % or less, 0.03 area % or less, or 0.02 area % or less of a henicosapentaenoic acid alkyl ester such as ethyl henicosapentaenoate;

0.1 area % or less, 0.05 area % or less, or 0.03 area % or less of a docosahexaenoic acid alkyl ester such as ethyl docosahexaenoate;

0.2 area % or less, 0.15 area % or less, 0.1 area % or less, 0.05 area % or less, or 0.02 area % or less of an a-linolenic acid alkyl ester such as ethyl a-linolenate.

Another embodiment of the present invention also encompasses an eicosapentaenoic acid alkyl ester-containing composition which, upon measurement by gas chromatography, comprises 96-99 area % of an eicosapentaenoic acid alkyl ester, wherein the content of an arachidonic acid alkyl ester is 0.1 area % or less. As already mentioned above, the eicosapentaenoic acid alkyl ester such as EPA-E tends to be difficult to separate from the arachidonic acid alkyl ester of similar structure such as ARA-E in the refining step. Of these two compounds which are in such a relationship that they are difficult to separate from each other, the eicosapentaenoic acid alkyl ester as the end product is contained in the composition of the embodiment under consideration at high levels of at least 96-99 area % whereas the content of the unintended arachidonic acid alkyl ester is extremely low, i.e., 0.1 area % or less. Thus, the effect of the arachidonic acid alkyl ester is extremely small in the composition under consideration, which can therefore be preferably used in applications that require high contents of the eicosapentaenoic acid alkyl ester. In the composition of the embodiment under consideration, the content of mono-trans forms of the eicosapentaenoic acid alkyl ester may be 10 area % or less, 5.0 area % or less, 3.0 area % or less, 2.5 area % or less, 2.0 area % or less, 1.8 area % or less, or 1.5 area % or less.

<Methods for Producing Compositions>

One embodiment of the present invention involves a method for producing a high-concentration eicosapentaenoic acid alkyl ester-containing composition, which comprises performing rectification on an eicosapentaenoic acid alkyl ester-containing composition with the degree of vacuum being 0.2 Torr or less and at a whole-column temperature of 190° C. or less, and performing a concentration treatment on the rectified composition using chromatography, the eicosapentaenoic acid alkyl ester-containing composition being obtained by alkyl esterifying a feed oil containing eicosapentaenoic acid; the method may comprise other steps as required.

Another embodiment of the present invention involves a method for producing high-concentration ethyl eicosapentaenoate by ethyl esterifying a feed oil containing eicosapentaenoic acid and thereafter performing distillation and chromatography, wherein the distillation is carried out by performing rectification with the degree of vacuum being 0.2 Torr or less and at a whole-column temperature of 190° C. or less, whereby the content of ethyl arachidonate is reduced while suppressing the generation of trans forms due to heat.

As described herein with respect to the methods of production involved in the above-described embodiments of the present invention, the step of performing distillation is sometimes simply referred to as the distillation step and the step of performing chromatography is sometimes simply referred to as the chromatographic step. It should also be noted that as described herein, the distillation step and the chromatographic step are sometimes collectively referred to as the refining step.

As the feed for the present invention, oils and fats or phospholipids that contain eicosapentaenoic acid as a constituent fatty acid, and so on may be used. Eicosapentaenoic acid is known to be contained abundantly in microorganism oils, marine animal oils, and so on. The feed oil may specifically be exemplified by: marine animal oils from fishes such as sardine, tuna, bonito, etc. and crustaceans such as hill; oils derived from lipid-producing microorganisms including yeasts such as the genus *Yarrowia*, filamentous fungi such as the genus *Mortierella*, algae such as the genus *Euglena*, and Stramenopiles. These may be oils derived from genetically modified microorganisms introduced with genes such as genetically modified mutant 49 elongase. Even these microorganism oils involve the same problem to deal with since they contain not only EPA but also fatty acids of carbon number 20 such as arachidonic acid. In addition, genetically modified plant derived oils from oil seed plants such as species of the genus *Brassica*, sunflower, maize, cotton, flax, and safflower that have been introduced with genes such as mutant Δ9 elongase by recombination technology can also be used as the feed oil. Genetically modified plant oils and genetically modified microorganism oils, etc. may be illustrated by those described, for example, in WO2012/027698, WO2010/033753, and so on.

For example, fish oils contain EPA as a triglyceride that consists of one molecule of glycerol to which three molecules of the fatty acid are linked to form an ester linkage. Since fish oils contain many kinds of fatty acids ranging from 14 to 22 in carbon number and from 0 to 6 in the number of double bonds, the concentration of EPA is limited. Hence, by means of alkyl esterification in which the fatty acid linked to the triglyceride is reacted with a lower alcohol in the presence of a catalyst or an enzyme, for example, by ethyl esterification involving reaction with ethanol, the fatty acid is separated from glycerin and, thereafter, fatty acid alkyl esters other than EPA alkyl esters such as EPA-E are removed to thereby produce high-purity EPA alkyl esters such as EPA-E. The production method in one mode of the present invention may also involve providing an EPA alkyl ester as obtained by such alkyl esterification, i.e., preparing a feed oil and esterifying the feed oil with a lower alcohol to obtain an EPA alkyl ester (which is hereinafter sometimes referred to as the esterification step.)

Crude Oil Refining Step

The feed oil to be used in the alkyl esterification may be a crude oil or it may be refined oil. The crude oil may be oils or fats obtained from fishery starting materials or may be oils or fats obtained from microorganism starting materials. For example, crude oils may be obtained from fishery starting materials by any method and in the case of fish oils, they are usually collected by the following method. Fish either in its entirety or as remains like its head, skin, backbone and guts that result from fish processing are ground, steamed and then pressed to separate stickwater from pressed meals. The oil or fat as obtained together with the stickwater is separated by centrifugation and recovered as crude fish oil.

Crude fish oils are generally subjected to the degumming step, the deacidifying step, the decolorizing step using activated clay or activated charcoal, the washing step, the deodorizing step as by steam distillation, and other steps depending on the feed and subjected to a refining process to remove any unintended substances such as phospholipids and sterols, thus yielding a refined fish oil. In one mode of the present invention, such refined fish oil can also be used as the feed.

Esterification Step

The oil or fat as the feed oil is subjected to alcoholysis using a lower alcohol, whereupon it is decomposed to a lower alcohol ester. Exemplary lower alcohols include those which are commonly used in the alkyl esterification of fatty acids, as exemplified by a lower alcohol having carbon number 1 or carbon number 2. In alcoholysis, a lower alcohol such as ethanol and a catalyst or an enzyme are added to the oil or fat, whereupon reaction occurs to generate an ethyl ester from the fatty acid linked to glycerin. Examples of the catalyst that can be used include an alkali catalyst, an acid catalyst, and the like. Lipase is used as the enzyme.

It has been shown empirically that the reaction efficiency of alcoholysis of fatty acids is high and after the alcoholysis, compositions are obtained that mainly contain those fatty acids which are in alkyl ester forms. Hence, unless otherwise noted herein, those fatty acids after the esterification step are sometimes denoted without indicating that they are fatty acids in alkyl ester forms. This, however, should not be taken as a total exclusion of the presence of fatty acids in forms other than the alkyl ester forms.

Refining Process

The production of a composition in one embodiment of the present invention comprises a process of refining by the distillation step and the chromatographic step using chromatography such as high-performance liquid chromatography (HPLC). It is noted here that EPA-E and ethyl arachidonate, for example, have similar molecular structures but have slightly different molecular weights, so they might be separable by distillation with the precision enhanced by making use of the difference in boiling point (EPA-E, 417° C./760 mmHg; ethyl arachidonate, 418.1° C./760 mmHg). From this viewpoint, it would be necessary to use more stages and/or increase the reflux flow in order to enhance the degree of separation. However, using more stages will lead to an increased pressure resistance and the distillation temperature has to be raised. Similarly, an increase in the reflux flow will also result in a raised distillation temperature. On the other hand, EPA is known to isomerize with heat (European Journal of Lipid Science and Technology, 108 (2006) 589-597; JAOCS, 66 (1989) 1822-1830). Hence, further heating to enhance the precision of distillation will cause isomerization and the amount of isomers will increase. Thus, it has been extremely difficult to prevent the generation of EPA-E isomers or keep their generation at low levels so that EPA alkyl esters such as EPA-E and arachidonic acid alkyl esters such as ethyl arachidonate can be separated on an industrial basis, namely, with both yield and purity being satisfied.

The distillation process described in JP H5-222392A is not capable of separating EPA-E and ethyl arachidonate since it is intended to collect C20 fractions. By the subsequent HPLC-based refining step, EPA-E and ethyl arachidonate can be separated to some extent but in order to obtain EPA-E of high purity, the overlap between EPA-E and ethyl arachidonate has to be cut off and the efficiency of EPA-E recovery drops considerably. In fact, in JP H5-222392A, FIG. 2 shows that EPA-E fractions were considerably cut off and even when EPA was purified to 99% and more, C20:4 ethyl esters including ethyl arachidonate were observed as impurities (paragraph [0033]). What is more, the recovery of EPA in this Example was as low as 60% and industrial production of EPA-E with a substantial decrease of ethyl arachidonate was impossible.

Given this situation and in the case where a crude product of an alkyl ester form like the ethyl ester form obtained in the above-described esterification step is to be distilled along with the method described in JP H5-222392A, etc., the method for producing a composition in one mode of the present invention performs rectification (precision distillation) by holding such pressure and temperature conditions that the degree of vacuum is 0.2 Torr (26.7 Pa) or less and the whole-column temperature is 190° C. or less, thus enabling EPA-E and ethyl arachidonate to be separated without considerably increasing the generation of isomers due to heat.

As regards the pressure and temperature conditions, by considering such factors as the drop in pressure resistance, the selection of vacuum pump types, the combination of vacuum pumps, it is possible to hold the degree of vacuum at 0.2 Ton or less and the whole-column temperature at 190° C. or less. Means for reducing the pressure resistance include, for example, increasing the diameter of pipes and connecting pipes at angles that provide a smooth joint. Since the boiling points of substances drop as the pressure decreases, distillation can be performed at lower temperatures when high vacuum (low pressure) prevails, and this makes it possible to suppress the denaturation of substances due to heat. On the other hand, a lowered boiling point increases the propensity to distillation and the reflux flow can be increased. By adjusting the conditions for rectification such that the degree of vacuum is at 0.2 Torr or less and the whole-column temperature is at 190° C. or less, rectification can be performed at even lower temperatures and with an adequate reflux flow. The increased reflux flow improves the precision of separation by distillation and separation from substances such as arachidonic acid alkyl esters that have boiling points close to those of EPA alkyl esters can also be accomplished easily. As a result, from the viewpoint of striking the balance between the two requirements, i.e., separation from other fatty acid alkyl esters like arachidonic acid alkyl esters and suppression of the generation of impurities due to heat, compositions having higher contents of EPA alkyl esters can be obtained.

As used herein, the term "rectification" refers to a technique in which part of the vapor generated under heating conditions is returned as reflux to the same distillation column and separation of components is performed with high precision by making use of the gas-liquid equilibrium between the vapor ascending through the column and the sample in a liquid state (JP H4-128250A and JP H5-222392A).

The term "whole-column" as used herein regarding the pressure and temperature conditions in the distillation step means that the conditions are associated with all distillation columns that can be used in the distillation step. If only one distillation column is used in the distillation step, the term means that the conditions are associated with that single distillation column, and if there is more than one distillation column that is used in the distillation step, the term means that the conditions are associated with said all distillation columns that are present.

The distillation step may be performed using a single distillation column; alternatively, it may be continuous rectification using two or more, three or more, or even four or more distillation columns. In continuous rectification using two or more distillation columns, it is particularly important to maintain the degree of vacuum. Since the supply of the feed into a vacuum and the withdrawal of fractions or residue can cause variations in the degree of vacuum, continuous production under high vacuum is preferably performed as variations in the degree of vacuum are suppressed by taking care to ensure that the degree of vacuum is maintained at a stable level. In continuous distillation to be performed using preferably three or more distillation columns, more preferably four or more distillation columns, the whole-tower degree of vacuum can be adjusted to 0.2 Torr or less. By lowering the degree of vacuum, the temperature can be further lowered. From an industrial viewpoint involving the need to install facilities of higher performance, continuous distillation is preferably performed at temperatures of 150-190° C., preferably at 170-190° C.

The HPLC- or otherwise based chromatographic step subsequent to the distillation step is a step in which the contents of any unintended components in the composition obtained in the distillation step are reduced by removing or otherwise treating the unintended components, so that EPA alkyl esters in the composition after rectification are further concentrated; this step can be performed along a conventionally known method, for example, the method described in JP HS-222392A, etc. As the chromatography to be used in the concentration treatment, reverse-phased chromatography is suited. The stationary phase is not particularly specified and any adsorbent for the reverse-phase distribution system can be used; a preferred example is an ODS column using octadecylsilyl (ODS).

Since the content of arachidonic acid alkyl esters can be reduced in the distillation step, the percent cut of EPA alkyl esters by HPLC is improved and their percent recovery is sufficiently enhanced to enable the production on an industrial scale of EPA alkyl esters with smaller contents of arachidonic acid alkyl esters and other impurities. As a further advantage, according to the method under consideration, it is possible to reduce the contents of impurities other than arachidonic acid alkyl esters including lower alkyl ester forms of C20:0, C20:4n-3, C20:5n-3(5,9,11,14,17), C18:3n-3, C18:4n-3, C19:0, C19:5n-3, C21:5n-3, and C22:6n-3—these have heretofore been difficult to separate—as well as mono-trans isomers of EPA alkyl esters like mono-trans isomers of EPA-E.

<Modes of Use>

The mode of using the composition in one embodiment of the present invention is not particularly limited but it is preferably in an oral dosage form, typically assuming the mode of oral formulations including granules, tablets, capsules, liquids/solutions, etc. Applications of the composition of the present invention include, for example, foods and drinks (e.g. health foods, neutraceutical foods, foods for specified health use (FOSHU), supplements, dairy products, soft drinks, pet foods or drinks, and feeds for domesticated animals), pharmaceuticals, quasi-drugs, and so on; supplements and pharmaceuticals are particularly preferred. In addition to use as food ingredients or foods per se, the composition may be used as a component to be added to feeds for animals. Therefore, the composition in one mode of the present invention can be used as an ingredient or an effective component of the above-mentioned foods and drinks, pharmaceuticals, and quasi-drugs and can preferably be used in their manufacture.

<Pharmaceutical Composition>

Another embodiment of the present invention involves a pharmaceutical composition containing the above-described composition as an effective component. The content of the above-described composition in the pharmaceutical composition is not particularly limited but it is preferably 25 wt % or above, more preferably 50 wt % or above, even more preferably 70 wt % or above, still more preferably 85 wt % or above, yet more preferably 96 wt % or above, and most preferably 98 wt % or above.

The pharmaceutical composition can be used to treat or prevent diseases including arteriosclerosis, cerebral infarct, cardiovascular infarct, thrombosis, lifestyle-related diseases such as hyperlipidemia, allergies, inflammatory diseases, and cancers; it may, for example, be used as a therapeutic agent for occlusive arteriosclerosis or as a therapeutic agent for hyperlipidemia.

Since the composition in one mode of the present invention is reduced in the content of impurities, it has an extremely high level of safety and can be used to prepare pharmaceutical preparations featuring a wide safety margin. For example, one can produce high-purity EPA ethyl ester preparations such as high-purity EPA-E preparations wherein the daily dose of EPA-E is at least three times, preferably at least five times its usual dose, or high-purity EPA ethyl ester preparations such as high-purity EPA-E preparations wherein the daily dose of EPA-E is at least 6 g, preferably at least 10 g. With the use of these preparations, even diseases for which no therapeutic efficacy can be expected from the usual doses in hyperlipidemia, etc. can safely be treated.

In addition to the effective component, the pharmaceutical composition in one mode of the present invention can comprise pharmaceutically acceptable additive components. The pharmaceutical composition comprising such additive components can comprise a pharmaceutically acceptable excipient. The pharmaceutical composition may appropriately incorporate therein known antioxidants, coating agents, gelling agents, flavoring agents, odorizers, preservatives, antioxidants, emulsifiers, pH modifiers, buffers, coloring agents, etc. As the antioxidant, at least one member selected from among butylated hydroxytoluene, butylated hydroxyanisole, propyl gallate, gallic acid, pharmaceutically acceptable quinones, ascorbic acid esters such as palmitate ascorbate, and tocopherols is desirably contained as the antioxidant in an effective amount.

The dosage form of the preparations is also variable with the form in which the effective component is used in combination and is not particularly limited, but oral preparations are preferred and exemplary forms that can be used include tablets, film coated tablets, capsules, microcapsules, granules, subtilized granules, powders, liquid preparations for oral administration, syrups, jellies, and inhalations. Particularly preferred is the oral administration of capsules prepared by encapsulation with, for example, soft capsules or microcapsules. The preparations may be orally administered as enteric or extended-release preparations or they may be orally administered as jellies to patients under dialysis, patients having difficulty in swallowing, and like patients. The pharmaceutical composition of the present invention can be produced or formulated into preparations in accordance with routine procedures.

One embodiment of the present invention involves a method of disease prevention, treatment, or relief comprising administering a pharmaceutical composition in another embodiment of the present invention to a subject who is affected or at a risk of being affected with at least one disease selected from the group consisting of arteriosclerosis, cerebral infarct, cardiovascular infarct, thrombosis, lifestyle-related diseases, allergies, inflammatory diseases, and cancers. The mode of administration may be oral administration or topical administration. The dosage may be a therapeutically or prophylactically effective amount and is set as appropriate for such conditions as the type of the target disease, the severity of the symptoms, the age, body weight and health state of the subject to which the composition is to be administered. In the case of an adult, for example, the composition of interest can be administered either orally or parenterally at a dose of 1 mg to 1 g/kg/day, preferably 5 mg to 300 mg/kg/day in terms of the amount of the effective component once or twice to four times a day, or divided in more portions, at appropriate intervals.

As used herein, the term "therapeutic agent" refers to a pharmaceutical which, in the case where a symptom due to the target disease is evident, is used to suppress or mitigate the progress of such disease. In contrast, the term "prophylactic agent" refers to a pharmaceutical which, in the case where the onset of a symptom due to the target disease is anticipated, is used to suppress that symptom by being administered in advance. It should, however, be noted that these terms may be used in combination depending on the timing of use or the symptom at the time of use and no limitative interpretation is intended.

As referred to herein, an element tagged with the indefinite article "a" or "an" does not exclude the possibility for the existence of one or more elements unless there is a clear indication or connection in the context. Hence, the indefinite article "a" or "an" usually means "at least one."

The verb "comprising" and its conjugation that are recited herein are used in a non-limitative sense and mean that the items following this term are included and that items that are not particularly mentioned are not excluded.

Individual invention-specifying features that are explained herein in one embodiment concerning each aspect of the present invention may be combined in any desired way to formulate a new embodiment and it should be understood that even such a new embodiment can be encompassed in each aspect of the present invention.

EXAMPLES

The present invention will be described below more specifically by reference to Examples but the present invention is by no means limited by these Examples. It should be noted that in the following Examples, unless otherwise specified, "%" means "wt %".

In the Examples and Comparative Examples in the following sections, EPA-E is used as an EPA alkyl ester but the present invention is not limited thereto and it may be replaced by other EPA alkyl esters such as EPA-M.

It has been shown empirically that the percent ethyl esterification of fish oils using ethanol is generally 95% to 100%. Hence, the starting material ethyl ester (fish oil ethyl ester) described in the section of the present Examples was presumably such that almost all of the saturated or unsaturated fatty acids contained were in the fatty acid ethyl ester form. Therefore, in the section of the present Examples, the saturated or unsaturated fatty acids contained in the feed oil will all be described as saturated or unsaturated fatty acids in the ethyl ester form. This, however, should be not taken to totally exclude the presence of fatty acids other than the ethyl ester form.

Example 1

<Method of Preparation>
A fish oil ethyl ester prepared in the usual manner (EPA in fatty acids≥16 area %; acid value≤0.8; POV≤30) was subjected to continuous rectification using a multi-stage distillation apparatus under such whole-column conditions that the degree of vacuum was 0.2 Torr or less and the temperature was 190° C. or less, whereupon the feed was fractionated into an initial fraction, a main fraction, and a residual fraction. The resulting main fraction was refined by high-performance liquid column chromatography (HPLC) using a column packed with an octadecylated silica gel of a reverse-phased distribution system, whereupon purified EPA-E was obtained.

<Method of Evaluation>
Using different starting materials, 11 lots of purified EPA-E were produced and analyzed for the makeup of fatty acids using gas chromatography (GC). The mean retention times for the peaks of respective fatty acid ethyl esters, their relative retention times, the average contents, maxima, and minima (area %) are shown in Table 1. The relative retention times indicated in Table 1 refer to the mean retention times for the respective peaks, with the mean retention time of EPA-E being taken as 1.

The GC measurement conditions used for analyzing the makeup of fatty acids were as follows:

GC-FID Measurement Conditions
  GC: 6890N (Agilent Technologies)
    Column: DB-WAX (Agilent Technologies)
      30 m×0.25 mm ID, 0.25 μm in film thickness
    Carrier gas: helium, 0.5 mL/min (so adjusted that EPA-E would elute in ca. 30 min)
  Injection port: 300° C., 1 μL, Split (1:100)
    Column temperature: 200° C. (constant)
  Detector: FID, 300° C.
  Makeup gas: nitrogen 40 mL/min.

TABLE 1

| | Mean retention time (min) | Relative retention time | Minimum value (area %) | Maximum value (area %) | Average value (area %) |
|---|---|---|---|---|---|
| EPA-E | 29.333 | 1.000 | 96.477 | 97.603 | 97.155 |
| Ethyl arachidonate | 23.571 | 0.804 | 0.044 | 0.208 | 0.090 |
| Isomer A (14-position trans form) | 28.010 | 0.955 | 0.256 | 0.339 | 0.290 |
| Isomer B (17-position trans form) | 30.138 | 1.027 | 0.262 | 0.369 | 0.312 |
| Isomer C (5-position trans form) | 31.146 | 1.062 | 0.231 | 0.295 | 0.265 |
| Isomer D (11-position trans form) + Isomer E (structure yet to be identified) | 31.591 | 1.077 | 0.668 | 0.965 | 0.820 |
| C18: 3n-3 ethyl ester | 14.197 | 0.484 | 0.036 | 0.098 | 0.060 |
| C18: 4n-3 ethyl ester | 15.385 | 0.524 | 0.062 | 0.185 | 0.116 |
| C19: 0 ethyl ester | 12.936 | 0.441 | 0.012 | 0.076 | 0.049 |
| C19: 5n-3 ethyl ester | 21.658 | 0.738 | 0.049 | 0.153 | 0.098 |
| C20: 0 ethyl ester | 17.062 | 0.582 | 0.014 | 0.087 | 0.038 |
| C20: 4n-3 ethyl ester | 26.968 | 0.919 | 0.089 | 0.374 | 0.174 |
| C20: 5n-3(5, 9, 11, 14, 17) ethyl ester | 40.286 | 1.373 | 0.059 | 0.161 | 0.086 |
| C21: 5n-3 ethyl ester | 38.862 | 1.325 | 0.029 | 0.133 | 0.086 |
| C22: 6n-3 ethyl ester | 55.389 | 1.888 | 0.029 | 0.075 | 0.050 |

As for Isomers A-D, isomer samples produced by forced heating were used to identify the makeup of isomers by GC-FID, determine the number of double bonds of respective peaks by GC-MS, and perform NMR analysis of respective peaks. As a result, it was verified that Isomers A-D were each an isomer of EPA-E in which only one of 14-, 17-, 5- and 11-positions of the five double bonds in EPA-E assumed a trans form. Since the peaks of Isomer D and Isomer E overlapped and were unable to separate, the amount of Isomer D was cited as the sum with the amount of Isomer E.

<Results of Evaluation>

By performing rectification with the whole-column degree of vacuum and temperature adjusted to 0.2 Torr or less and 190° C. or less, respectively, the contents of difficult-to-separate impurities such as ethyl arachidonate, C20:0 ethyl ester, C20:4n-3 ethyl ester, C20:5n-3(5, 9, 11, 14, 17) ethyl ester, C18:3n-3 ethyl ester, C18:4n-3 ethyl ester, C19:0 ethyl ester, C19:5n-3 ethyl ester, C21:5n-3 ethyl ester, and C22:6n-3 ethyl ester could be reduced while at the same time, the contents of trans isomers of EPA-E could also be reduced. What is more, the contents of MUFA ethyl ester and DHA ethyl ester in the resulting compositions were each 0.05 area % or less.

By carrying out ODS-column based HPLC after the rectification, eicosapentaenoic acid alkyl ester-containing compositions were obtained that contained 96-99 area % of ethyl eicosapentaenoate, with the ethyl arachidonate content being 0.7 area % or less and the content of mono-trans forms of ethyl eicosapentaenoate being 2.5 area % or less.

In the present invention, it has been found that one can produce compositions in which eicosapentaenoic acid alkyl esters such as ethyl eicosapentaenoate are contained at high purities whereas the contents of impurities are further reduced as compared to the conventional levels. As the composition in one mode of the present invention can even be produced on an industrial scale, it can advantageously be used as a starting material for health foods, pharmaceuticals, etc. that need be mass-produced while having the safety feature.

The disclosure of Japanese Patent Application No. 2014-188997 filed on Sep. 17, 2014 is incorporated herein in its entirety by reference.

All documents, patent applications and technical standards described herein are incorporated herein by reference to the same extent as the case where it has been noted specifically and individually that the individual documents, patent applications and technical standards are incorporated by reference.

The invention claimed is:

1. An eicosapentaenoic acid alkyl ester-containing composition which, upon measurement by gas chromatography, comprises 96 to 99 area % of an eicosapentaenoic acid alkyl ester, wherein the content of alkyl esters of saturated fatty acids is 0.5 area % or less, and wherein the composition satisfies at least one of the following (i)-(iv):
   (i) the sum of the contents of alkyl esters of n-3 fatty acids having a carbon number of 18 to 22, other than the eicosapentaenoic acid alkyl ester, is 2.0 area % or less,
   (ii) the content of an octadecatetraenoic acid (C18:4 n-3) alkyl ester is 0.4 area % or less,
   (iii) the content of a nonadecapentaenoic acid (C19:5 n-3) alkyl ester is 0.2 area % or less, and
   (iv) the content of an eicosatetraenoic acid (C20:4 n-3) alkyl ester is 0.7 area % or less.

2. The composition of claim 1, wherein the content of mono-trans forms of the eicosapentaenoic acid alkyl ester is 2.5 area % or less.

3. The composition of claim 1, wherein the sum of the contents of mono-trans forms and di-trans forms of the eicosapentaenoic acid alkyl ester is 2.5 area % or less.

4. The composition of claim 1, wherein the sum of the contents of mono-trans forms, di-trans forms and tri-trans forms of the eicosapentaenoic acid alkyl ester is 2.5 area % or less.

5. The composition of claim 1, wherein the sum of the contents of mono-trans forms, di-trans forms, tri-trans forms and tetra-trans forms of the eicosapentaenoic acid alkyl ester is 2.5 area % or less.

6. The composition of claim 1, wherein the content of any one of the mono-trans forms of the eicosapentaenoic acid alkyl ester in which any one of the double bonds at 5-position, 14-position, and 17-position thereof is trans is 0.5 area % or less.

7. The composition of claim 1, wherein the content of a mono-trans form of the eicosapentaenoic acid alkyl ester in which the double bond at 11-position thereof is trans is 1.0 area % or less.

8. The composition of claim 1, wherein the content of an arachidonic acid alkyl ester is 0.7 area % or less.

9. The composition of claim 1, wherein the content of a n-nonadecanoic acid (C19:0) alkyl ester is 0.1 area % or less.

10. The composition of claim 1, wherein the content of an arachidic acid (C20:0) alkyl ester is 0.2 area % or less.

11. The composition of claim 1, wherein the content of a-linolenic acid (C18:3 n-3) alkyl ester is 0.2 area % or less.

12. The composition of claim 1, wherein the content of an icosa-5,9,11,14,17-pentaenoic acid (C20:5 n-3(5,9,11,14, 17)) alkyl ester is 0.2 area % or less.

13. The composition of claim 1, wherein the content of a henicosapentaenoic acid (C21:5 n-3) alkyl ester is 0.2 area % or less.

14. The composition of claim 1, wherein the content of docosahexaenoic acid (C22:6 n-3) alkyl ester is 0.1 area % or less.

* * * * *